United States Patent [19]

Verbicky, Jr. et al.

[11] Patent Number: 4,554,357

[45] Date of Patent: Nov. 19, 1985

[54] BIS-QUATERNARY SALTS AS PHASE TRANSFER CATALYSTS FOR AROMATIC ETHER IMIDE PREPARATION

[75] Inventors: John W. Verbicky, Jr., Scotia; Elbridge A. O'Neil, Jr., Port Henry, both of N.Y.

[73] Assignee: General Electric Company, Schenectady, N.Y.

[21] Appl. No.: 542,242

[22] Filed: Oct. 14, 1983

Related U.S. Application Data

[63] Continuation-in-part of Ser. No. 527,617, Aug. 29, 1983, abandoned.

[51] Int. Cl.$^4$ ............... C07D 209/48; C07D 403/10; C07D 403/12
[52] U.S. Cl. .................... 548/461; 548/473; 548/474; 548/476; 548/477; 548/480; 548/478; 548/481; 548/181; 548/138; 548/336; 546/272; 544/332
[58] Field of Search ............... 548/461, 473, 476, 474, 548/477, 478, 480, 481

[56] References Cited

U.S. PATENT DOCUMENTS 3,992,432 11/1976 Napier et al. .................... 260/465.1
4,273,712 6/1981 Williams, III ....................... 548/461

OTHER PUBLICATIONS

Nakayama, *Bull. Chem. Soc. Japan,* 52(1), 52–56 (1974).
Horner, et al., *Werkstoffe & Korrosion,* 30, 413–417 (1979).

*Primary Examiner*—Donald G. Daus
*Assistant Examiner*—William A. Teoli, Jr.
*Attorney, Agent, or Firm*—William H. Pittman; James C. Davis, Jr.; James Magee, Jr.

[57] ABSTRACT

Bis-quaternary ammonium and phosphonium salts such as bis(tri-n-butyl)-1,6-hexylenediammonium dibromide are excellent phase transfer agents for the preparation of aromatic ether imides, as by the reaction of the disodium salt of bisphenol A with 4-nitro-N-methylphthalimide.

12 Claims, No Drawings

BIS-QUATERNARY SALTS AS PHASE TRANSFER CATALYSTS FOR AROMATIC ETHER IMIDE PREPARATION

This application is a continuation-in-part of copending application Ser. No. 527,617, filed Aug. 29, 1983, now abandoned.

This invention relates to the preparation of aromatic ether imides, and more particularly to improved phase transfer catalysts for use in said preparation.

Aromatic ether imides are a known class of compounds. It is also known that various aromatic ether bisimides such as 2,2-bis[4-(3,4-dicarboxyphenoxy)phenyl]propane bis-N-methylimide may be converted to dianhydrides, which in turn may be reacted with diamines to produce polyetherimides. Certain bisimides can also be reacted directly with diamines to produce polyetherimides, as disclosed and claimed in copending, commonly assigned application Ser. No. 505,636, filed June 20, 1983. The analogous monoimides and the corresponding monoanhydrides can be used, for example, as end-capping or chain-stopping agents for polyetherimides.

A convenient method of preparing aromatic ether imides is by the nucleophilic displacement reaction of a substituted aromatic imide, such as a substituted phthalimide, wherein the substituents may be, for example, halo or nitro, with an alkali metal salt of a hydroxyaromatic compound. This reaction is often conveniently effected in solution in a substantially non-polar organic solvent, in the presence of a phase transfer catalyst. U.S. Pat. 4,273,712 describes suitable reaction conditions and the use of various quaternary ammonium and phosphonium salts as phase transfer catalysts; its disclosure is incorporated by reference herein.

It is frequently found that a relatively large amount of quaternary ammonium or phosphonium salt must be used as a phase transfer catalyst in the displacement reaction, in order for it to proceed rapidly enough to produce the ether imide in an economically feasible time period. Moreover, a portion of the phase transfer catalyst is usually converted to nitrosamine by-products during the reaction; said by-products are, for the most part, insoluble in water and remain in the ether imide product even after washing with water and/or aqueous base. It is of interest, therefore, to develop phase transfer catalysts which can be used in smaller proportions in the reaction and which generate either no nitrosamines or water-soluble nitrosamines which can be easily removed during the aqueous wash steps.

A principal object of the present invention, therefore, is to provide an improved method for the preparation of aromatic ether imides by the reaction of substituted aromatic imides with alkali metal phenoxides.

A further object is to provide improved phase transfer catalysts for use in said reaction.

Still another object is to provide phase transfer catalysts which can be used in very small quantities and generate either no nitrosamine by-products or nitrosamines which are easily removed from the product.

Other objects will in part be obvious and will in part appear hereinafter.

In its broadest sense, the present invention comprises an improvement in a method for preparing an aromatic ether imide by the reaction, in a non-polar organic solvent in the presence of a phase transfer catalyst, of (A) at least one hydroxyaromatic compound alkali metal salt having the formula (I)  $R^1(OM)_a$, wherein $R^1$ is an aromatic radical containing about 6–30 carbon atoms, M is an alkali metal and a is 1 or 2, with (B) at least one substituted imide having the formula

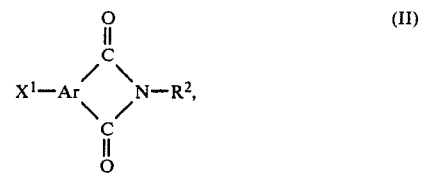

(II)

wherein Ar is an aromatic radical, $R^2$ is hydrogen or a hydrocarbon-based radical containing about 1–13 carbon atoms and $X^1$ is halo or nitro;

said improvement comprising using as said phase transfer agent (C) at least one bis-quaternary salt having the formula $$(R^4)_k Q^{\oplus}(R^3)_m {}^{\oplus}Q(R^4)_k (X^{2\ominus})_2, \quad (III)$$

wherein each $R^3$ is independently a divalent hydrocarbon-based radical and all $R^3$ radicals taken together contain about 4–12 carbon atoms, each $R^4$ is independently a lower hydrocarbon-based radical, Q is nitrogen or phosphorus, $X^2$ is an anion-forming atom or radical, k is an integer from 1 to 3, and m is 4–k; at least three of $R^3$ and $R^4$ radicals attached to each Q atom being aliphatic or alicyclic.

Reagent A in the method of this invention is at least one alkali metal salt of a mono- or dihydroxyaromatic compound, depending on whether a is 1 or 2. The M value may be any alkali metal; it is usually lithium, sodium or potassium and preferably sodium.

The $R^1$ value may be any aromatic radical containing about 6–30 carbon atoms. It may be a hydrocarbon radical or may contain other atoms such as oxygen or sulfur. Illustrative monovalent radicals (i.e., those derived from compounds in which a is 1) include phenyl, m-tolyl, p-tolyl, 1-naphthyl, 2-naphthyl, p-chlorophenyl and 4-bromo-1-naphthyl.

Most often, $R^1$ is a divalent aromatic radical; i.e., a is 2. Illustrative radicals of this type are derived from such compounds as resorcinol, hydroquinone, 4,4'-dihydroxybiphenyl, 4,4'-dihydroxy-3,3',5,5'-tetramethylbiphenyl, 4,4'-dihydroxydiphenylmethane, 3,4'-dihydroxydiphenylmethane, 2,2-bis(2-hydroxyphenyl)propane, 2,2-bis(4-hydroxyphenyl)propane (hereinafter "bisphenol A"), 2-(3-hydroxyphenyl)-2(4-hydroxyphenyl)propane, 1,1-bis(4-hydroxyphenyl)ethane, 2,2-bis(4-hydroxyphenyl)pentane, 4,4'-dihydroxybenzophenone, bis(4-hydroxyphenyl)ether, bis(4-hydroxyphenyl sulfide, bis(4-hydroxyphenyl)sulfoxide, bis(4-hydroxyphenyl)sulfone and 3-hydroxyphenyl 4-hydroxyphenyl sulfone.

The following radicals are preferred as $R^1$:

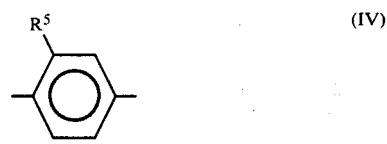

(IV)

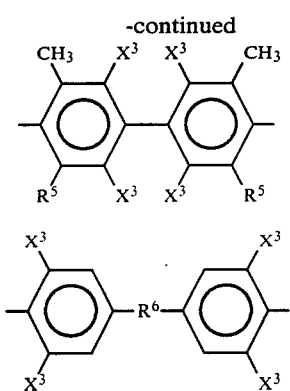

wherein each $R^5$ is independently hydrogen or methyl, $R^6$ is a straight-chain or branched alkylene radical containing 1–5 carbon atoms and is most often the isopropylidene radical, and each $X^3$ is independently hydrogen or halogen (usually chlorine or bromine). Mixtures of the foregoing formulas are also contemplated. Especially desirable is the radical derived from bisphenol A by the removal of both hydroxy groups therefrom, and having formula VI wherein $R^6$ is isopropylidene and each $X^3$ is hydrogen.

The Ar value in reagent B may be any aromatic radical which contains about 6–30 carbon atoms and which is capable of forming an imide. In general, these are radicals derived from o-dicarboxylic acids such as phthalic acid and 2,3-naphthalenedicarboxylic acid; however, radicals derived from acids such as 1,8-naphthalenedicarboxylic acid are also suitable. Most preferably, Ar is derived from phthalic acid; i.e., it is the o-phenylene radical. The $X^1$ substituents thereon are halo (usually fluoro or chloro) or, preferably, nitro.

The $R^2$ value is hydrogen or a hydrocarbon-based radical containing from 1 to about 13 carbon atoms. The term "hydrocarbon-based radical" as used herein denotes a radical having a carbon atom directly attached to the remainder of the molecule and having predominantly hydrocarbon character within the context of this invention. Such radicals include the following:

(1) Hydrocarbon radicals, which may be aliphatic [e.g., methyl, n-propyl, isopropyl, n-butyl, 1-pentyl, 2-pentyl, 1-hexyl, 1-(4-decenyl)], aromatic (e.g., phenyl, p-tolyl, 1-naphthyl, 2-naphthyl), alicyclic (e.g., cyclopentyl, cyclohexyl), aromatic- or alicyclic-substituted aliphatic, aliphatic-substituted aromatic, or the like.

(2) Substituted hydrocarbon radicals; that is, radicals containing non-hydrocarbon substituents which, in the context of this invention, do not alter the predominantly hydrocarbon character of the radical. Those skilled in the art will be aware of suitable substituents (e.g., nitro, alkoxy, carbalkoxy).

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

A preferred subgenus of $R^2$ radicals consists of alkyl and especially lower alkyl radicals, the term "lower" denoting not more than 7 carbon atoms. The preferred lower alkyl radical is methyl.

A second preferred subgenus consists of electron-deficient radicals. For the most part, these comprise aromatic hydrocarbon radicals containing one or more strongly electron-withdrawing substituents and heterocyclic radicals having aromatic character. Compounds in which $R^2$ is of this type are disclosed and claimed in the aforementioned application Ser. No. 505,636, the disclosure of which is incorporated by reference herein.

Suitable aromatic hydrocarbon radicals include phenyl, naphthyl and the like containing such substituents as halo, nitro, keto, carbalkoxy, cyano and perfluoroalkyl. At least one of said electron-withdrawing substituents is preferably ortho or para to the free valence bond (i.e., the one attached to the imide nitrogen atom). The trifluoromethylphenyl radicals are particularly preferred.

Suitable heterocyclic radicals having aromatic character include those with 5- or 6-membered rings and aromatic unsaturation of the type existing in pyrrole and pyridine. These radicals preferably contain 1–3 and especially 1 or 2 hetero atoms of which at least one is nitrogen and the others, if present, are nitrogen or sulfur. They are usually unsubstituted but may be substituted, especially with electron-withdrawing substituents such as those previously enumerated. The free valence bond is preferably in the 2- or 4-position with respect to a hetero atom. If the ring contains more than one hetero atom, and especially if it is 5-membered, the free valence bond is preferably attached to the single carbon atom between two of said hetero atoms.

Illustrative 5-membered heterocyclic radicals are pyrrolyl, 2-thiazolyl, 2-imidazolyl and 2-(1,3,4-thiadiazolyl). Illustrative 6-membered radicals are 2-pyridyl, 3-pyridyl, 4-pyridyl, 2-pyrimidyl, 2-pyrazyl, 2-(1,4-thiazolyl) and 2-(1,3-thiazolyl). Particularly preferred heterocyclic radicals are the aminopyridyl radicals, especially 2-pyridyl and 4-pyridyl.

Reagent C, the phase transfer catalyst, is at least one bis-quaternary salt having formula III. In that formula, each $R^3$ is independently a divalent hydrocarbon-based radical; it may be an aliphatic (usually alkylene), alicyclic (usually cycloalkylene) or aromatic radical such as ethylene, propylene, trimethylene, tetramethylene, hexamethylene, octamethylene, decamethylene, dodecamethylene, cyclohexylene, phenylene, tolylene or naphthylene, or a divalent heterocyclic radical derived from a compound such as pyridine or indole. Most often, the $R^3$ radicals are alkylene. The carbon content of all the $R^3$ radicals taken together is about 4–12 carbon atoms, and each $R^3$ radical ordinarily contains at least about 4 carbon atoms. Preferably, only one $R^3$ radical is present (i.e., m is 1 and each k is 3) and it contains about 5–10 and most desirably 6 carbon atoms.

Each $R^4$ radical is a lower hydrocarbon-based radical. Illustrative $R^4$ radicals are methyl, ethyl, n-propyl, isopropyl, n-butyl, isobutyl, n-hexyl, n-heptyl, cyclopentyl, cyclohexyl, methylcyclohexyl, phenyl, tolyl, 2-(1,4-dioxanyl) and 2-furyl. Preferably, the $R^4$ radicals are all alkyl, especially n-alkyl radicals with 4–6 carbon atoms.

The Q value may be nitrogen or phosphorus and is usually nitrogen. The $X^2$ value may be any anion which is stable under the conditions of the invention; suitable anions include chloride, bromide, sulfate, p-toluenesulfonate and methanesulfonate. Because of the ready availability and particular suitability of bromide reagents for the preparation of reagent C as described hereinafter, $X^2$ is usually bromide.

The value of the integer k may be from 1 to 3, and the value of m is 4-k. Most often, each k is 3 and m is 1.

According to this invention, the $R^3$ and $R^4$ radicals are chosen so that at least three thereof attached to each Q atom are aliphatic or alicyclic, most often aliphatic. Thus, no more than one such radical is aromatic or heterocyclic. In the most preferred compounds, all of the $R^3$ nd $R^4$ radicals are aliphatic.

Illustrative bis-quaternary salts which may be used as reagent C are those in which $R^3$ is a polymethylene chain from trimethylene to dodecamethylene, each $R^4$ is either n-butyl or n-hexyl, Q is nitrogen, $X^2$ is bromide, each k is 2 and m is 2; the compound in which each $R^3$ is ethylene, $R^4$ is n-butyl, Q is nitrogen, $X^2$ is bromide, each k is 1 and m is 3; and the compound in which $R^3$ is hexamethylene, each $R^4$ is n-butyl, Q is phosphorus, $X^2$ is bromide, each k is 3 and m is 1. Other suitable compounds will be readily apparent to those skilled in the art. The preferred compound is bis(tri-n-butyl)-1,6-hexylenediammonium dibromide.

The bis-quaternary salts useful as reagent C may be prepared by known methods, typically by the reaction of a suitable tertiary amine or tertiary phosphine with a carbonium ion-generating compound. It is usually most convenient to react a bis-carbonium ion-generating compound, typically an alkylene dichloride, dibromide, bis-methanesulfonate or the like, with a tertiary monoamine or monophosphine. However, a diamine or diphosphine can also be reacted with a mono-carbonium ion-generating compound such as an alkyl bromide; this route is frequently preferred when m is more than 1, such as for the preparation of bis-quaternary salts derived from 1,4-diazabicyclo[2.2.2]octane (triethylenediamine).

The preparation of bis-quaternary salts useful as reagent C is illustrated by the following examples.

EXAMPLE 1

A solution of 21.6 grams (0.1 mole) of 1,4-dibromobutane and 37 grams (0.2 mole) of tri-n-butylamine in 63 ml. of acetonitrile was heated under reflux for 16 hours. Volatiles were removed by distillation and the oily residue was recrystallized from o-dichlorobenzene. The product was the desired bis(tri-n-butyl)-1,4-butylenediammonium dibromide having a melting point of 151° C.

EXAMPLE 2

The procedure of Example 1 was repeated, substituting 0.05 mole of 1,10-dibromodecane for the 1,4-dibromobutane and using 0.1 mole of tri-n-butylamine. The oily residue was the desired bis(tri-n-butyl)-1,10-decylenediammonium dibromide.

EXAMPLE 3

Following the procedure of Example 2, bis(tri-n-hexyl)-1,10-decylenediammonium dibromide was prepared by the reaction of tri-n-hexylamine with 1,10-dibromodecane.

EXAMPLE 4

A mixture of 11.95 grams (0.048 mole) of 1,6-dibromohexane, 18.05 grams (0.0975 mole) of tri-n-butylamine and 30 grams of acetonitrile was heated under reflux for 24 hours, after which volatiles were removed by vacuum stripping. Toluene, 25 ml., was added and the mixture was cooled until a crystalline product separated. The crystals were filtered, washed twice with pentane and dried. The product was the desired bis(tri-n-butyl)-1,6-hexylenediammonium dibromide.

EXAMPLE 5

Following the procedure of Example 1, 0.1 mole of 1,4-diazabicyclo[2.2.2]octane was reacted with 0.2 mole of n-butyl bromide. The product was the desired N,N'-di-n-butyl-1,4-diazabicyclo[2.2.2]octane dibromide.

EXAMPLE 6

A solution of 20.23 grams (0.1 mole) of tri-n-butylphosphine and 12.2 grams (0.05 mole) of 1,6-dibromohexane in 35 grams of acetonitrile was heated under reflux for 24 hours. Volatile materials were removed by vacuum evaporation and the solid product, the desired bis(tri-n-butyl)-1,6-hexylenephosphonium dibromide, was slurried in pentane, filtered, washed with pentane and dried under vacuum.

According to the present invention, the reaction between reagents A and B is ordinarily effected at a temperature within the range of about 25°–150° C., preferably about 100°–120° C., in a non-polar organic solvent such as benzene, toluene, xylene, chlorobenzene, o-dichlorobenzene, tetrahydrofuran, acetonitrile, octane or the like. It is preferred to use approximately equivalent amounts of the two reagents, which includes the use of a slight excess (usually no more than about 5 mole percent) of either.

Reagent C is usually present in the reaction mixture in the amount of about 0.005–2.0 equivalents per equivalent of reagent A. (For the purposes of this invention, the equivalent weight of reagent A is its molecular weight divided by the number of aromatic hydroxy groups present therein, and that of reagent C is half its molecular weight.) It is seldom necessary, however, to use more than about 0.2 equivalent of phase transfer catalyst per equivalent of reagent A. Since a characteristic of the present invention is that reagent C may be used in very small amounts, the preferred concentration range thereof is about 0.005–0.04 equivalent per equivalent of reagent A.

Also contemplated as part of the invention are compositions comprising (A) at least one hydroxyaromatic compound alkali metal salt, (B) at least one substituted imide and (C) at least one bis-quaternary salt, all as previously defined herein, preferably in the above-described proportions. Said compositions are useful for conversion to aromatic ether imides by the previously described reaction.

The method of this invention is illustrated by the following example.

EXAMPLE 7

Various amounts of bis-quaternary salts were added as phase transfer catalysts to a mixture of 1.5 grams (0.0055 mole) of bisphenol A disodium salt, 2.27 grams (0.011 mole) of 4-nitro-N-methylphthalimide, 5.7 grams of toluene and 0.31 gram of o-terphenyl (used as an internal standard). The mixtures were heated to reflux and sampled periodically, with the progress of the reaction and the yield of 2,2-bis[4-(3,4-dicarboxyphenoxy)-phenyl]propane bis-N-methylimide being followed by liquid chromatography. The results are listed in the following table.

| Bis-quaternary salt of Example | Equivs. per equiv. of Bisphenol A salt | Time, hrs. | Yield of bisimide, % |
|---|---|---|---|
| 1 | 0.04 | 0.5 | 37 |
|   |      | 1.0 | 48 |
|   |      | 2.0 | 75 |
| 2 | 0.01 | 0.5 | 84 |
|   |      | 1.0 | 91 |
|   |      | 2.0 | 98 |
|   | 0.007 | 0.5 | 84 |
|   |      | 1.0 | 92 |
|   |      | 2.0 | 96 |
| 3 | 0.02 | 0.5 | 86 |
|   |      | 1.0 | 94 |
| 4 | 0.01 | 0.5 | 70 |
|   |      | 1.0 | 91 |
|   |      | 2.0 | 98 |
|   |      | 3.0 | 99 |

The results in the table show the effectiveness of the bis-quaternary salts as phase transfer catalysts. Another advantage of the method of this invention is that mass spectrometric analysis showed no evidence of nitrosamine formation during the reaction.

What is claimed is:

1. In a method for preparing an aromatic ether imide by the reaction, in a non-polar organic solvent in the presence of a phase transfer catalyst, of (A) at least one hydroxyaromatic alkali metal salt having the formula $$R^1(OM)_a, \qquad (I)$$

where $R^1$ is an aromatic radical having about 6–30 carbon atoms, M is an alkali metal and a is 1 or 2, with (B) at least one substituted imide having the formula

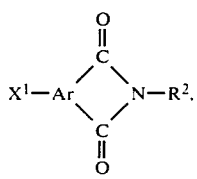
(II)

wherein Ar is an aromatic radical, $R^2$ is hydrogen or a hydrocarbon-based radical having about 1–13 carbon atoms and $X^1$ is halo or nitro;

the improvement which comprises using as said phase transfer catalyst (C) at least one bis-quaternary salt having the formula $$(R^4)_k{}^\oplus Q(R^3)_m{}^\oplus Q(R^4)_k(X^{2\ominus})_2, \qquad (III)$$

wherein each $R^3$ is independently a divalent hydrocarbon-based radical and all $R^3$ radicals taken together have about 4–12 carbon atoms, each $R^4$ is independently an n-alkyl radical having 4–6 carbon atoms, Q is nitrogen or phosphorus, $X^2$ is an anion-forming atom or radical, k is an integer from 1 to 3, and m is 4-k; at least three of the $R^3$ and $R^4$ radicals attached to each Q atom being aliphatic or alicyclic.

2. A method according to claim 1 wherein the hydroxyaromatic compound is bisphenol A and reagent B is a substituted phthalimide.

3. A method according to claim 2 wherein Q is nitrogen.

4. A method according to claim 3 wherein m is 1 and each k is 3.

5. A method according to claim 4 wherein $R^3$ is an alkylene radical having about 5–10 carbon atoms.

6. A method according to claim 5 wherein reagent C is present in the amount of about 0.005–0.04 equivalent per equivalent of reagent A.

7. A method according to claim 6 wherein M is sodium and $X^1$ is nitro.

8. A method according to claim 7 wherein $R^2$ is a lower alkyl radical.

9. A method according to claim 8 wherein $R^2$ is methyl.

10. A method according to claim 9 wherein reagent C is bis(tri-n-butyl)-1,6-hexylenediammonium dibromide.

11. A method according to claim 1 wherein $R^2$ is an electron-deficient radical.

12. A method according to claim 11 wherein reagent C is bis(tri-n-butyl)-1,6-hexylenediammonium dibromide.

* * * * *